(12) United States Patent
Husek

(10) Patent No.: US 6,770,246 B1
(45) Date of Patent: Aug. 3, 2004

(54) SORBENT CARTRIDGE FOR SOLID PHASE EXTRACTION

(75) Inventor: Petr Husek, Prague (CZ)

(73) Assignee: Phenomenex, Inc., Torrance, CA (US)

( * ) Notice: Subject to any disclaimer, the term of this patent is extended or adjusted under 35 U.S.C. 154(b) by 0 days.

(21) Appl. No.: 09/518,342

(22) Filed: Mar. 3, 2000

(51) Int. Cl.⁷ .................................................. B01L 11/00

(52) U.S. Cl. .................... 422/101; 73/864.01; 210/263; 210/504; 436/178

(58) Field of Search ................................. 422/100, 101, 422/63, 69, 88, 919, 922; 210/490, 506, 446, 502.1, 504, 263, 266; 73/863.21, 863.23, 863.32, 864.01, 864.11, 864.13; 436/178

(56) References Cited

U.S. PATENT DOCUMENTS

| | | | |
|---|---|---|---|
| 2,806,509 A | * 9/1957 | Bozzacco et al. | ............. 109/80 |
| 3,985,032 A | * 10/1976 | Avakian | .................. 73/863.25 |
| 4,138,474 A | * 2/1979 | Updike | ........................ 210/504 |
| 4,774,058 A | * 9/1988 | Mehl | .......................... 210/266 |
| 4,999,164 A | 3/1991 | Puchinger | |
| 5,156,811 A | * 10/1992 | White | |
| 5,332,426 A | * 7/1994 | Tang et al. | ................. 55/385.3 |
| 5,437,979 A | * 8/1995 | Rampal et al. | ................. 435/6 |
| 6,048,457 A | * 4/2000 | Kopaciewicz et al. | ... 210/321.6 |
| 6,057,165 A | * 5/2000 | Mansour | ..................... 436/518 |
| 6,165,519 A | * 12/2000 | Lehrer et al. | ............... 210/501 |
| 6,200,474 B1 | * 3/2001 | Kopaciewicz et al. | ... 210/321.6 |
| 6,566,145 B2 | * 5/2003 | Brewer | ....................... 436/178 |

FOREIGN PATENT DOCUMENTS

| | | |
|---|---|---|
| DE | 3717211 A1 | * 12/1988 |
| GB | 2158057 A | * 11/1985 |

OTHER PUBLICATIONS

Merriam–Webster's Collegiate Dictionary (10th ed., p. 1092 for definition of silica gel).*
Hawley's Condensed Chemical Dictionary (Lewis, Richard J. Sr, 13th ed., p. 34 for definition of alkyd resins).*
Globe Scientific online catalog (http://www.globescientific.com/cpage30.html, pp. 1–3).*
Bromage, et al. "Examination of micro–tip reversed–phase liquid chromatographic extraction of peptide pools for mass spectrometric analysis". *Journal of Chromatography A*, issue 826, p. 167–181, published by Elsevier Science B. V. 1998.
Published U.S. patent application No. US 2003/0039589, published Feb. 27, 2003; Smith, J.C.

* cited by examiner

*Primary Examiner*—Joseph Drodge
(74) *Attorney, Agent, or Firm*—Stetina Brunda Garred & Brucker

(57) ABSTRACT

An improved sorbent cartridge for use in preparing fluid samples by solid phase extraction for chemical analysis is provided that uses a pipette having a longitudinal axis and a tip having walls defining a uniformly tapered interior cavity extending along the axis and opening at a distal end of the tip. A porous barrier is placed in the tapered cavity at a predetermined location in the tip to define a sorbent volume between the barrier, the cavity walls and the opening at the distal end of the tip. The barrier allows processing fluids to pass through the barrier while retaining the sorbent. A slurry of sorbent material is drawn into the sorbent volume by a syringe in fluid communication with the pipette tip. The solvent is drawn through the barrier, filing the sorbent volume with sorbent material. A serum to be analyzed is similarly drawn into the sorbent through the opening in the distal end of the tip, by applying a suction to the tip. After interacting with the sorbent material, the serum is further drawn through the barrier into the syringe and removed for analysis or use.

49 Claims, 1 Drawing Sheet

SORBENT CARTRIDGE FOR SOLID PHASE EXTRACTION

BACKGROUND OF INVENTION

The present invention relates to a sorbent cartridge especially useful for solid phase extraction but having applicability in other areas. Solid Phase Extraction (SPE) is a widely used sample preparation/purification technique applied for complex samples such as natural product extracts and body fluids. This technique uses small separation columns (cartridges) which contain a layer of sorbent material. The components of a sample passed through this layer of sorbent material are either retained on the surface of the sorbent material or pass through the sorbent material unretained. The nature of the sorbent material is usually chosen such that the components of interest are retained in the sorbent cartridge and those that pass through are either not of interest, or the failure to be absorbed indicates the absence of a particular component. The absorbed component is released during a later processing step for subsequent processing and/or analysis.

Commercially available SPE cartridges are available in various sizes, usually with an internal diameter of 5 mm and up, an internal volume of minimum 1 ml and contain 100–200 mg of sorbent material. In exceptional cases such cartridges can hold 25–50 mg of sorbent. Recently released SPE equipment operates plastic plates with 96 wells, each well containing 10–15 mg of sorbent material.

SPE cartridges are made by placing a first porous disk or glass or silicone wool at the bottom of the cartridge and then filling the sorbent material from top of the cartridge. The layer of sorbent material is kept in place with a second porous disk placed on top of the sorbent material. During use, the fluid sample, the wash and the extraction fluids are passed through the SPE cartridge from top to bottom, i.e. in the direction of gravitational forces. The fluid sample penetrates through the layer of sorbent material due to gravitation or centrifugation, or because of pressure or vacuum applied to the cartridge with various accessories, but the direction of flow is along the direction of gravity from the top to the bottom and then out an opening in the bottom.

SUMMARY OF INVENTION

An improved sorbent cartridge for use in preparing fluid samples for chemical analysis is provided by placing sorbent into a pipette tip at its distal end and sucking fluid to be analyzed into the sorbent with a setter. This mode of use reverses the fluid flow of a normal sorbent cartridge. The sorbent cartridge is formed from a pipette tip having a longitudinal axis and a tip with tapered interior having walls defining a cavity extending along the axis and opening at a distal end of the tip. A porous barrier is placed in the tapered cavity at a predetermined location in the tip to define a sorbent volume between the barrier, the cavity walls and the opening at the distal end of the tip. The barrier allows processing fluids to pass through the barrier. A sorbent material is placed in the sorbent volume. The sorbent material is preferably selected for use in chemical analysis and the barrier being selected to prevent passage of the sorbent material. This construction is adapted for use by applying a reduced pressure to draw or suck the fluid to be analyzed against the direction of gravity, through the tip of the pipette, through the sorbent and then through the barrier filter. This cartridge is especially suitable for preparing samples for chromatographic analysis, but has broader applicability.

Variations to this basic sorbent cartridge can be made. These variations include the addition of means for exerting suction on the pipette to draw processing fluids through the opening in the tip, through the sorbent material and through the filter. A manually operated syringe structure or a pipette can achieve this. The syringe preferably comprises a setter in fluid communication with a second opening opposite the opening in the distal end. The setter is configured to mate with the second opening to place a first cavity in the setter in fluid communication with the filter. A plunger is slidably received in a second cavity in the setter and placed in fluid communication with the first cavity. The plunger and first cavity are sized relative to each other so as to create a suction sufficient to draw fluid from the opening in the tip into the cavity in the setter when the plunger slides in the second cavity.

Preferably, the size of the opening in the tip is from about 2 to about 10 times the size of the material used in the sorbent material. Further, the sorbent material is placed in the cartridge by drawing a mixture of a solvent and the sorbent material through the opening in the distal end of the tip, with the solvent passing through the filter to leave the sorbent in the sorbent volume. The sorbent material itself preferably has a coating of a solvent that is sticky enough to cause sorbent material to stick together and resist passage out of the opening in the tip. The solvent is preferably one of glycol or ethylene glycol, which do not adversely affect most analytical methods.

Advantageously, the sorbent volume comprises a tapered volume tapered toward the distal opening, and the porous barrier comprises a frusto-conical filter of similar shape, aligned to fit into and wedge into the tapered volume.

Another aspect of this invention comprises an apparatus for analysis of fluid samples, preferably for use in chromatography. The apparatus comprises a hollow tip having an opening in a distal end and means in the tip for retaining a porous barrier at a predetermined location to define a sorbent volume between the barrier and the opening in the hollow tip. A sorbent material is retained in the sorbent volume by the porous barrier, with the barrier allowing passage of fluids but not the sorbent material, during use of the apparatus. Suction means are placed in fluid communication with the hollow tip to suck fluid through the opening in the distal end and through the sorbent material and porous barrier.

The invention further comprises a method of forming a sorbent cartridge. A porous barrier is placed at a predetermined location in a hollow tip of a pipette to define a sorbent volume between the barrier and opening in a distal end of the tip. A slurry of sorbent and a fluid is sucked or drawn into the sorbent volume through the opening in the distal end of the tip until the volume is filled with sorbent. The solvent is further sucked through the barrier while the barrier prevents passage of the sorbent. The solvent is selected so that it does not degrade later use of the sorbent for chemical analysis. This method advantageously allows the fast formation of a sorbent cartridge with a high accuracy of the sorbent volume.

This basic method is further varied by sucking a washing fluid through the opening, sorbent and barrier to remove undesired materials from the sorbent. Additionally, at least one cap can be placed on the tip to help prevent degrading the performance of the sorbent. The method further comprises the step of placing a syringe suction device in fluid communication with the tip to exert a reduced pressure that draws fluids through the opening, sorbent and barrier and into the syringe. Alternatively, the method can comprise the step of placing a syringe device in fluid communication with the tip to exert a positive pressure that forces fluids through the barrier, sorbent and opening. As with the apparatus, the method preferably leaves a coating on the sorbent that causes the sorbent material to stick to each other and resist falling out of the opening. That coating is achieved by using a solvent selected from the group comprising glycol and ethylene glycol.

There is also provided an improved method of forming and using the sorbent cartridge for chemical analysis. This method allows easy formation followed by immediate use, which has advantages in some applications. This method comprises the steps of placing a porous barrier at a predetermined location in a hollow tip of a pipette to define a sorbent volume between the barrier and opening in a distal end of the tip and sucking a slurry of sorbent into the sorbent volume through the opening in the distal end of the tip until the volume is filled with sorbent and sucking the solvent through the barrier while the barrier prevents passage of the sorbent. The solvent is selected so that it does not degrade later use of the sorbent for chemical or chromatographic analysis. A fluid sample to be analyzed is then sucked through the opening and into the sorbent to interact with the sorbent. Most of the fluid sample is withdrawn through the barrier except for the components retained on the sorbent. Advantageously, the sample components retained on the sorbent can be extracted from the sorbent by passing another fluid thorough the sorbent, by collecting this fluid in the setter and by transferring it into a removable container for further analysis or processing. Alternatively, by applying a positive pressure through the barrier into the sorbent the sorbent can be expelled out the opening for further analysis or processing of the sorbent after it has interacted with the fluid sample. In this case the directing of fluid flow is in the direction of gravitational forces.

The above methods and apparatus provide many advantages. One advantage of this invention is to provide a sorbent cartridge, which is made of commercially available pipette tips, or a similar conical body holding a small volume of sorbent material in the tip.

Another advantage of this invention is to provide a cartridge used for SPE filled with a sorbent underneath a porous layer that keeps the sorbent material in place during the filling of the tip and after the tip has been filled.

Another advantage of this invention is to provide a cartridge, which may release the sorbent into a vial or reaction vessel for further sample preparation and/or analysis.

Another advantage of this invention is to provide a sorbent cartridge, which may be made by an automated sample preparation instrument right before use in the shortest time.

Another advantage of this invention is to provide a sorbent cartridge, which allows for small sample volumes to be prepared for analysis by requiring small amounts of reagents and by reducing sample dilution to minimum.

BRIEF DESCRIPTION OF THE DRAWING

These and other features, advantages and objectives of this invention will be better understood by reference to the following description and the drawings, in which like numbers refer to like parts throughout the description, and in which.

DETAILED DESCRIPTION

Figure 1:
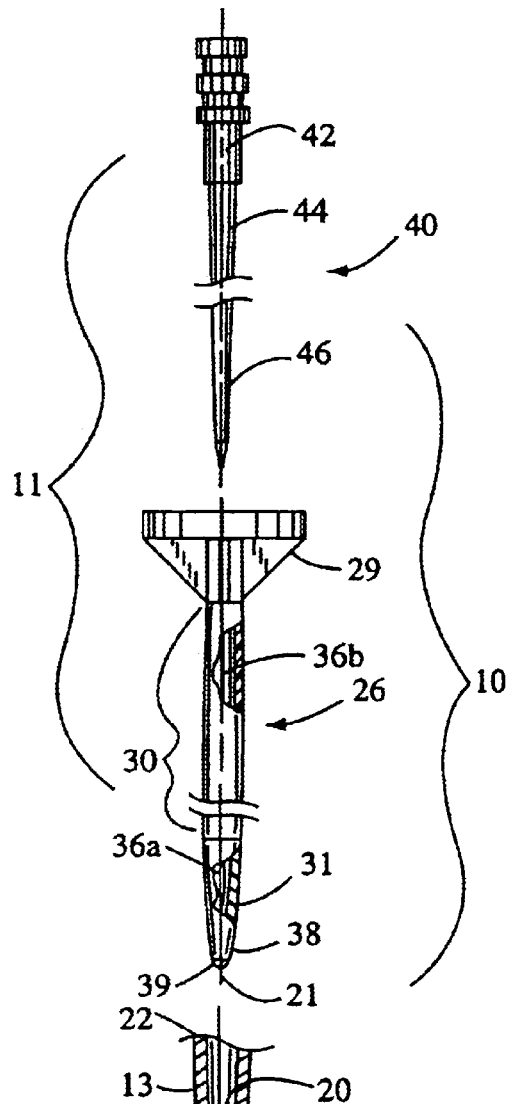
FIG. 1 is a perspective view of a pipette assembly of this invention.

Referring to FIG. 1, a pipette 10 has a tubular portion 11 ending in a distal, hollow tip 12. Such pipettes 10 are made out of plastic, usually polypropylene, and have volumes ranging between 10 microliter up to several milliliters. The hollow tip 12 defines a cavity into which a sorbent barrier is placed. The sorbent barrier prevents passage of a sorbent material but allows passage of fluid. As used herein, fluid comprises liquids and gases, but the primary and preferred use of this invention is with liquids. In the illustrated embodiment, the sorbent barrier comprises filter disk 14 placed in the tip 12. The filter disk 14 separates the cavity into a first, distal volume or space 16 between a distal end 18 of the tip 12, and the filter 14, and a second volume or space 20 located between the filter disk 14 and the entrance 22 of the pipette. The size of the spaces or volumes 16, and 20 will vary depending on the size and location of the filter 14 and also on the total volume of the pipette tip. Advantageously, the space 16 forms part of a tapered cavity extending along the length of the distal end 18 of pipette 10, with the taper being uniform and symmetric about a longitudinal axis 21 of the tip 12. In short, the volume 16 preferably forms a conical shaped hollow, although other cavity shapes can be used. An opening 19 is formed in the distal end 18.

A porous boundary is to retain the sorbent material 26 while allowing the fluids to pass. The form and composition of the porous boundary will vary with the configuration of the surrounding structure, but in the illustrated embodiment the porous boundary is achieved by filter disk 14. The size of the filter disk 14 is tailored such that it can be inserted into the pipette tip 12 up to a certain depth and frictionally engage the interior walls of the tip 12 to remain in position during use. The filter 14 is preferably inserted from the entrance 22 and urged toward the distal end 18. The filter 14 is preferably frusto-conical in shape, having a larger diameter and a smaller diameter, and preferably tapered at an angle that coincides with that of the tapered volume 16. It can be of variable length, but is preferably short, with a length of about 2 mm along the longitudinal axis 21 being believed suitable for smaller diameter filters 14. The filter 14 is configured or sized so that it wedges into place at a predetermined location in the tip 12, in order to provide a distal space 16 of a predetermined volume. Thus, the position of the filter 14 along the longitudinal axis 21 can determine the volume 16 in the tip 12. In this illustrated embodiment, the depth of penetration of the filter 14 along the longitudinal axis 21 thus depends on the diameter of the disk 14, which is used to limit the volume 16 to be filled with sorbent material. The filter 14 is preferably made of porous polyethylene, although it could be made of other porous materials such as glass wool.

Figure 2:
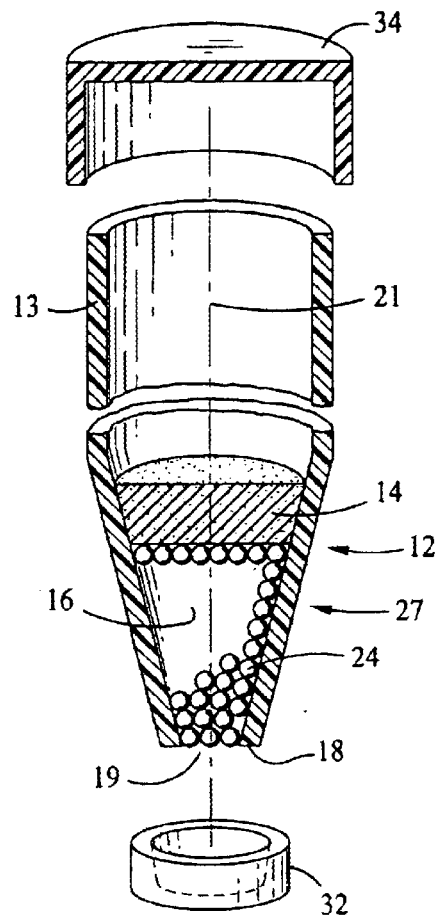
FIG. 2 is a partial sectional view of a tip of the assembly of FIG. 1.

In more detail, and referring to FIGS. 1–2, the positioning of the filter disk 14 along the longitudinal axis 21 of pipette tip 12 is precisely defined so that the volume 16 delimited by the filter disk 14, the walls of the pipette tip 12 and the distal end 18 of the pipette tip 12, are all controlled. This volume or space 16 defines the amount of sorbent material 24 that is held by the sorbent cartridge. This volume 16 advantageously ranges between 10 microliter up to 1 milliliter, although other volumes are possible but may require more customized pipette tips.

The filter 14 may be inserted into the pipette tip 10 by various ways that position the sorbent barrier, illustrated here by filter 14, at the desired location and that preferably fasten the filter 14 in position. Advantageously, the filter 14 is inserted by placing the larger end of the filter 14 onto a distal end 26 of setter 28 (FIG. 1) and inserting the setter 26 and filter 14 into the entrance of the pipette 10 until the filter wedges into the interior of the pipette tip 12. A narrow rod could also be used to push the filter 14 into position. If desired, markings on the setter 26 could be used in connection with the location of the opening 22 of the pipette 10, or a mark on the pipette 10, in order to indicate the appropriate insertion distance.

The tip 12 of the pipette 10, when fitted with filter 14 to define the distal volume 16, forms an empty sorbent cartridge 27.

The chemical nature of sorbent material 24 will vary with the sample to be analyzed. The sorbent material 24 typically comprises small, uniformly sized spherical media of silica or polymeric resin or other material onto which are bonded various chemical coatings. Preferably, the sorbent material 24 is added after the sorbent barrier, shown as filter 14, is positioned to define the distal volume 16. Preferably, the pipette 10 is placed onto the setter 26 similar to a needle placed onto a syringe. The setter 26 acts as a syringe body, and a plunger 40 acts as the plunger to exert a sufficiently low pressure or vacuum to draw fluid into the needle and syringe body. Before describing the use, a further description of the plunger 40 and setter 26 are provided.

Referring to FIG. 1, the setter 26 is tubular, with a cavity 36 extending along its longitudinal axis. The cavity 36 preferably forms a cylindrical cavity 36a for the length of the cylindrical outer diameter 30 and through the enlarged end 29. The cavity 36 preferably forms a tapered cavity 36b for the portion corresponding to the tapered end 31 of setter 26 and at the same taper angle. A distal end 38 of the setter 26 preferably has an opening 39 in communication with the cavity 36.

The plunger 40 is shaped to correspond with at least a part of the cavity 36, and preferably for all of it when the plunger 40 is inserted into the cavity 36. The plunger 40 has a handle 42 at one end. A central portion 44 of the plunger is cylindrical and sized to form a close fit with the cylindrical portion 36a of cavity 36, a fit tight enough to draw a vacuum as the plunger 40 is withdrawn from the cavity 36a. The other end 46 of plunger 40 is tapered, preferably to correspond to the tapered end 36b of cavity 36. The plunger 40 is shaped to act as a plunger for a syringe, with the setter 26 acting as the syringe. An enlarged end 29 can be placed on the setter 26 to make it easier to draw the vacuum by relative movement of the plunger 40 and setter 26.

To load sorbent 24 into the cavity 16, the distal end 18 of the pipette tip 12 is immersed into a mixture made of the appropriate sorbent material and a solvent. A heterogeneous mixture of a solid (sorbent) and a liquid (solvent) is also referred to as a slurry and that term will also be used herein. The plunger 40 is then slowly withdrawn from the syringe body (setter 26) causing the slurry to fill the volume 16 under the porous boundary formed by filter 14. The solvent from the mixture passes through the filter 14 while the sorbent 24 does not, thus allowing the sorbent 24 to accumulate below the filter in the volume 16. The plunger 40 is withdrawn until the space 16 under the porous boundary is completely filled with sorbent material at which time the distal end 18 is withdrawn from the slurry. The plunger 40 is further withdrawn and exerts further suction until the slurry liquid is evacuated from the accumulated sorbent bed contained in the volume 16. The plunger 40 and syringe (setter 26) can then be withdrawn from the pipette 10, as the suction from the plunger 40 maintains the slurry liquid in the body of the setter 26. The slurry liquid can then be discarded after removing the sorbent cartridge and by pushing the plunger 40 into the setter 26 to squirt the slurry liquid out the opening 39 in the distal end 38 of the setter 26. Next the setter (26) will be reinserted for immediate use. Such setters 26 and plungers 40 are commercially available for use with pipettes 10.

The sorbent cartridge 27 prepared in this manner may be used immediately or can be stored for later use. The solvent used for slurry preparation has to meet certain requirements in order to insure proper filling of the cartridge and also to prevent sorbent loss during storage and use. The slurry must not interfere with the intended use of the sorbent. Thus, the slurry solvent is preferably chemically inert with the intended chemicals used later with the sorbent or with the sample components interacting with the sorbent during use. To make filling easier, it is preferred that the sorbent has about the same density as the mixture solvent so the sorbent 24 floats in the solvent. Further, the slurry solvent preferably wets the sorbent. A slurry solvent with low vapor pressure, that does not quickly evaporate, is thus preferred. The slurry solvent also preferably makes the sorbent slightly sticky so the sorbent sticks and clumps together so it does not readily fall out of the opening 19 in the distal end 18 of the tip 12. Finally, the slurry solvent must pass through the sorbent barrier 14. Glycol or ethylene glycol are believed to be suitable slurry solvents for many sorbents.

Referring to FIG. 2, when the pipette 10 has the volume 16 filled with sorbent, a filled sorbent cartridge 27 is formed. Depending on the suction applied by the plunger 40, the sorbent 24 can be packed into the volume 16 to varying degrees. The sorbent 24 advantageously substantially fills all of the volume 16, and is packed tight enough so that sorbent 24 does not fall out of the opening 19 in the distal end 18 of the pipette tip 12. As mentioned above, using a solvent that leaves the sorbent slightly sticky can help the sorbent from unintentionally leaving the sorbent volume 16. The sorbent volume once filled will hold about 50–60% solid sorbent. The remaining portion of the sorbent volume 16 comprises the empty, interstitial space between the particles that comprise the sorbent 24. It is difficult to pack more than that amount of granular material in a volume without crushing the material. If less than that amount is packed in to the volume, the packing is so loose that it falls out.

The filled cartridges 27 may be capped at one or both ends 22 and 18 in order to preserve the sorbent bed for protracted periods of time. Suitable caps 32, 34 are illustrated schematically in FIG. 2, placed over the ends 18 and 22, respectively, although other forms of caps or sealants can be used. The caps can thus take various shapes such as the hollow, cup-like caps illustrated, and are made of material that does not affect the intended use of the sorbent 24. Polyethylene is one example of a cap material. The cap 34 over the end 22 of the pipette 10 is not needed if the plunger (setter 26) is inserted into the pipette 10, as the fit between the outer cylindrical portion 30 and the inner cylindrical portion 11 is close enough to form a seal.

Advantageously, commercially available pipette tips are used. It is preferable that the opening 22 to the pipette be standard size such that conventional commercially available pipettes, setters or automated liquid dispensing devices be attached to the sorbent cartridge 12. Further, it is preferable that the small opening 19 at the distal end 18 be slightly larger than normal to make it easier to load the sorbent slurry, with the size of the opening 19 in the end 18 varying depending on the nature of the sorbent 24 and in particular depending on the size of the media particles used in the sorbent.

The standard pipette tip has an opening in end 18 of 0.5 mm (0.02"). The preferred size of the opening 19 for the present application is about 0.8 mm (0.032"). The preferred opening 19 in end 18 is thus about 50% larger than the standard opening in the pipettes 10. This preferred size of opening 19 is about 3 to 10 times larger than the size of the sorbent material 24, which is typically comprised of generally uniformly sized spheres. Thus, it is preferred that the opening 19 be at least 2 time the size of the largest media used in the sorbent material 24, and preferably from 3 to 10 times larger. Larger sizes of opening 19 can be used, but with greater risk that the sorbent material 24 will fall out. If desired, a retainer frit or screen can be fastened over the end of the opening 19 after the sorbent material 24 is placed in the volume 16. But that hinders the ability to expel sorbent 24 from the sorbent volume 16 in some analytical applications.

The resulting pipette cartridge 27 has a small volume of sorbent 24 in the cartridge 27. The placement of that sorbent 24 in the pipette tip 12 makes it very easy to use. A description of one example of the use of this invention will help illustrate the advantages of the cartridge 27. The distal end 18 of a sorbent cartridge 27 is placed onto a setter 26 and the distal end 18 immersed into a sample of body fluid such as serum. A volume of sample is withdrawn by pulling on the plunger 40 to suck the serum into the cartridge 27. The suction causes the serum to pass thorough the layer of sorbent material 24 by slowly withdrawing the plunger 40 of the setter 26. The free amino acids present in the serum sample are retained on the surface of the sorbent material 24 in the cartridge 27 as the serum passes over the sorbent material. Once a sufficient sample is withdrawn and passed through the sorbent material 24, the distal end 18 is withdrawn from the serum. The plunger 40 is withdrawn enough to suck the serum through the sorbent material 24 and through the filter 14. The distal tip 38 of the setter 26 is adjacent the filter 14 and the serum passes into the cavity 36 in the body of the setter 26. The setter 26 and the remnants of the serum in the setter 26 can then be removed from the pipette 10. Pushing on the plunger 40 creates a positive pressure that causes the remnants of the serum to be expelled from the setter 26. The remnants of the serum can be discarded, or placed in a vial for further use, depending on the analytical process being used.

After discarding the remnants of the serum from the setter 26, the setter 26 may be immediately inserted in to the pipette 10 for subsequent use, or it may be washed by withdrawing the plunger 40 to suck a cleaning fluid into the cavity 36 of the setter 26 and then expelling the cleaning fluid by pushing on the plunger 40.

Next a washing solution is passed through the cartridge 28 by placing the distal end 18 in a washing solution and withdrawing the plunger 40 to suck the cleaning fluid through the sorbent bed 24, through the filter 14 and into the cavity 36 of the setter 26. The washing step is used to help remove sample droplets trapped between sorbent particles. The washing step can be repeated as needed.

In the next step of the illustrative process the amino acids retained on the sorbent material are released by extraction with an appropriate solvent. Thus, a solvent is drawn by suction into the cartridge 27, through the sorbent bed 24 to create an amino acid extract that passed through the filter 14 and into the cavity 36 of the setter 26. The amino acid extract is expelled from the cavity 36 of the setter 26 by pushing the plunger 40 to expel the extract from the opening 39 in the setter. The extract can be expelled into a vial or other desired receptacle or location for further analysis or for further preparation for analysis.

Alternatively, the extraction step may be performed in a vial after the sorbent material 24 is expelled from the cartridge 27 into the vial. This can be accomplished by filling some fluid into the cavity 36 of the setter 26, inserting the setter 26 into the pipette 10, depressing the plunger 40 to pass the fluid through the filter disk 14 toward the distal end 18 of the cartridge 27—which is in the opposite direction used to fill the cartridge. A sufficiently high positive pressure caused by the plunger 40, will expel the sorbent 24 out the opening 19 in the distal end 18 of the pipette tip 12, into the desired location or vial The use of readily available components such as the pipettes 10, setter 26 and plunger 40 provides a cost effective apparatus. Equally important is that the volume of the sorbent 24 can be accurately varied from very small volumes to much larger volumes. This allows the efficient use of small volumes of sample and sorbents. It also reduces waste; saves reagents used in subsequent sample preparation. The operation of the plunger 40, setter 26 and pipette 10 is easily achieved, and it allows manual control over the process. Further, while it is preferred that the sorbent bed 24 remain in the cartridge 27 and the various analytical chemicals be sucked through the bed by withdrawing plunger 40, it is possible to eject the sorbent bed 24 from the cartridge 27 for exhaustive extraction. This provides a versatile way of processing, or partially processing samples. Moreover, the preferred conical shape of the sorbent volume 16 is believed to provide efficient fluid flow as the fluid enters a small area and is drawn by reduced pressure to a larger surface on the upper end of the conical sorbent volume 16.

Figure 3:
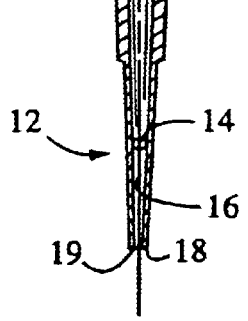
FIG. 3 is a partial sectional view of an alternate embodiment of the tip of the assembly of FIG. 1.
Figure 4:
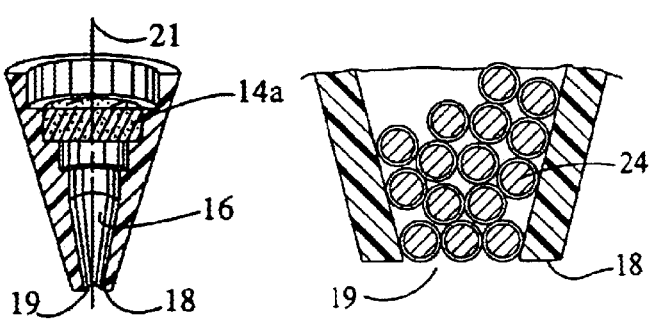
FIG. 4 is a partial sectional view of a tip assembly of FIG. 1 showing the sorbent with a stickey layer thereon.

The illustrated embodiment uses a tapered cavity to form the volume 16, and a conical filter 14 to form the porous barrier that retains the sorbent 24 while allowing fluids to pass. Other arrangements are possible. For example, referring to FIG. 3, the interior of the pipette tip 12 could comprise cylindrical segments having diameters that decrease toward the distal end 18 with a tapered, conical end at the distal end 18 of the pipette tip 12. A cylindrical filter 14a rests on the ledges formed by the steps to position the filter 14a along the longitudinal axis 21. By selecting the filter 14a of an appropriate diameter, the position of the filter along the axis 21 can be controlled. The steps can be located at predetermined intervals to make it easy to determine the volume 16 of the sorbent bed 24. The disadvantage of this construction is that it requires special manufacturing of the pipette tip 12, whereas the preferred embodiment uses conventional pipette tips 12 or slight variations of those pipette tips, and that helps reduce costs.

In the above embodiments, the opening 19 in the distal end 18 is smaller than the filter 14, 14a, and the cross-sectional area at the filter 14, 14a is larger than the cross-sectional area of the opening 19 in distal end 18 of the pipette tip 12. This results in a sorbent volume 16 that narrows toward the opening 19 in the distal end 18, with the narrowing preferably being a uniform taper, like in a cone. That narrowing causes the sorbent 24 to wedge toward the narrower opening 19 in distal end 18, which helps the sorbent 24 to stick together and not fall out the opening 19 under the influence of gravitational forces. The narrower opening 19 in the distal end 18 is also selected to hinder the sorbent 24 from falling out of the volume 16 under the influence of gravity. If a volume 16 is used that does not have a tapered shape, the volume 16 preferably still has a narrow opening in the distal end 18 to help retain the sorbent 24 in the volume 16, and preferably has at least a slight taper immediately adjacent that opening in distal end 18 to provide a slight wedging action on the sorbent 24. As described above, the size of the opening 19 in the distal end 18 is has to be larger than the largest particle in the sorbent 24 in order for the sorbent to enter the volume 16, but the opening is preferably only a few times larger than the largest dimension of the particles comprising the sorbent 24 as that helps hinder the particles from falling out of the volume 16 under the force of gravity.

The above methods and apparatus provide many advantages. The sorbent cartridge 27 can be made of commercially available pipette tips or a similar conical body holding a small volume of sorbent material in the pipette tip, although preferably slight modifications are made to the pipette tips as described herein. The use of commonly available parts, or modifications of such commonly available parts, reduces costs while allowing a high repeatability and accuracy of the sorbent volume 16. It should be understood, however, that other shapes of the tip 12, sorbent volume 16 and filter 14 can be used other than the preferred conical shapes.

Another advantage of this invention is to provide a cartridge 27 especially suitable for SPE that is filled with a sorbent underneath a porous layer 14 that keeps the sorbent material 24 in place during the filling of the tip 12 and after the tip has been filled. The location of the porous layer 14 on an interior end of the sorbent volume 16 and the passage of the fluid in a direction away from the opening 19 in the distal end of the distal end 18, which is normally opposite the direction of gravity, also provides a simple and accurate way to achieve a sorbent cartridge 27.

Another advantage of this invention is to provide a cartridge, which may release the sorbent into a vial or reaction vessel for further sample preparation and/or analysis. The use of the plunger 40 to draw fluids through the sorbent 24 and into a removable syringe (cavity 36 of setter 26) provides an easy and readily accessible way to prepare samples for testing and analysis. Further, by pushing on the plunger 40 the sorbent 24 can be expelled from the tip 12 for collection and use in chemical analysis. The manually operated plunger 40 and syringe (setter 26) also provide an inexpensive yet readily available means for manually controlling the formation of the sorbent cartridge 27, and the passage of fluids through the sorbent cartridge for analysis and removal.

Another advantage of this invention is to provide a sorbent cartridge, which may be made by an automated sample preparation instrument right before use in the shortest time. It is believed possible to draw in the slurry containing the sorbent and form the sorbent cartridge 27 in less than a minute. After discarding the solvent used in the slurry, which takes only moments, the sorbent cartridge 27 is ready for immediate use. The time to form the sorbent cartridge 27, less than a minute, is a very short time. That short time provides great flexibility as well as significant savings of labor and associated costs.

The above description is given by way of example, and not limitation. Given the above disclosure, one skilled in the art could devise variations that are within the scope and spirit of the invention, including various sequences of sucking in processing fluids through the sorbent bed 24 and expelling fluids through the sorbent bed 24. Also, it is believed possible, but not preferable, to place the sorbent 24 into the space 12 from the opening 22 rather than the opening 19 in end 18, and then place the filter 14 into position with any excess sorbent material 24 being forced out the opening in the end 18. Further, while this invention is described using a manually operated suction means, preferably in the form of a syringe, various motor driven suction devices and vacuum pumps could also be used, especially where the fluid is not desired to be retained for further analysis. Moreover, the various features of this invention can be used alone, or in varying combinations with each other and are not intended to be limited to the specific combination described herein. Thus, the invention is not to be limited by the illustrated embodiments but is to be defined by the following claims when read in the broadest reasonable manner to preserve the validity of the claims.

What is claimed is:

1. A sorbent cartridge for use in preparing samples for chemical analysis, comprising:

a pipette tip having a longitudinal axis and a hollow distal tip with tapered walls defining an interior cavity extending along the axis and having an opening at a distal end of the tip which opening is not covered by a porous barrier;

a porous barrier in the tapered cavity placed at a predetermined location in the tip to define a sorbent volume between the barrier, the cavity walls and the opening at the distal end of the tip, the barrier allowing processing fluids to pass through the barrier; and a sorbent material in the sorbent volume and extending from the opening toward the barrier, the sorbent material being selected for use in the chemical analysis and the porous barrier being selected to prevent passage of the sorbent material past the porous barrier and out of the sorbent volume, the sorbent material comprising a plurality of sorbent particles which are capable of being expelled through the opening in the distal end of the tip by pressure.

2. The sorbent cartridge of claim 1, further comprising a manually operated suction device on the pipette tip to exert a suction on the pipette tip to draw processing fluids through the opening in the tip, through the sorbent material and through the porous barrier.

3. The sorbent cartridge of claim 1, wherein the pipette tip has a second opening opposite the opening in the distal end, and further comprising a setter configured to mate with the second opening to place a first cavity in the setter in fluid communication with the porous barrier, the setter having a plunger slidably received in a second cavity in the setter and placed in fluid communication with the first cavity, the plunger and second cavity sized relative to each other so as to create a suction sufficient to draw fluid from the opening in the tip into the cavity in the setter when the plunger slides in the second cavity.

4. The sorbent cartridge of claim 1, wherein the sorbent material comprises a plurality of particles and the size of the opening in the tip is from about 2 to about 10 times the size of the particles used in the sorbent material.

5. The sorbent cartridge of claim 1, wherein the sorbent material is placed in the cartridge by drawing a slurry of a solvent and the sorbent material through the opening in the distal end of the tip, with the slurry solvent passing through the porous barrier to leave the sorbent in the sorbent volume.

6. The sorbent cartridge of claim 5, wherein the solvent is one of glycol, ethylene glycol or propylene.

7. The sorbent cartridge of claim 5, wherein the solvent includes a form of glycol.

8. The sorbent cartridge of claim 1, wherein the sorbent material comprises a plurality of particles with a coating of a solvent on the particles that is sticky enough to cause the particles to stick together and resist passage out of the opening in the tip under gravitational forces while allowing sorbent to be expelled under pressure.

9. The sorbent cartridge of claim 1, further comprising a removable cap covering the opening.

10. A sorbent cartridge, comprising:
   a pipette tip having an interior cavity in fluid communication with a distal opening located in the tip;
   a filter placed in the tip and defining a predetermined volume that extends between the filter and the distal opening with no further filter being in the predetermined volume; and
   a sorbent material substantially filling the volume, the filter retaining the sorbent material in the predetermined volume while allowing passage of processing fluids through the filter during use of the cartridge, the sorbent material comprising a plurality of particles which are capable of being expelled through the distal opening by pressure.

11. The sorbent cartridge defined in claim 10, wherein the pipette tip has a second opening adapted to removable receive a setter to draw fluid from the distal opening, through the sorbent material and filter into the setter.

12. The sorbent cartridge of claim 11, wherein the pipette tip contains a fluid drawn from the distal opening through the sorbent material and filter.

13. The sorbent cartridge of claim 10, wherein the predetermined volume is tapered toward the distal opening to form a frusto-conical shaped cavity and the filter comprises a frusto-conical filter.

14. The sorbent cartridge of claim 10, wherein the sorbent material comprises particles having diameters and wherein the distal opening has a diameter of about 2 to about 10 times the maximum diameter of the sorbent material.

15. The sorbent cartridge of claim 10, wherein the sorbent material comprises a plurality of particles having a coating of a solvent that is sticky enough to cause the particles of the sorbent material to stick together and resist passage out of the opening in the tip under the influence of gravitational forces while allowing sorbent to be expelled under pressure.

16. The sorbent cartridge of claim 15, wherein the solvent is one of glycol, ethylene glycol, or propylene.

17. The sorbent cartridge of claim 15, in the solvent includes a form of glycol.

18. A sorbent cartridge for use in preparing samples for chemical analysis, comprising:
   a hollow tip having an opening in a distal end;
   means in the tip for retaining a porous barrier at a predetermined location to define a sorbent volume between the barrier and the opening in the hollow tip, with no porous barrier being interposed between the opening and said means; and
   a sorbent material between the opening and said retained means in the sorbent volume by the porous barrier for use in the chemical analysis, the barrier allowing passage of fluids but not the sorbent material, during use of the sorbent cartridge, the sorbent material including a plurality of sorbent particles capable of being expelled out of the opening in the distal end by pressure.

19. The sorbent cartridge of claim 18, further comprising suction means in fluid communication with the hollow tip to suck fluid through the opening in the distal end and through the sorbent material and porous barrier.

20. The sorbent cartridge of claim 18, further comprising a removable cap covering the opening.

21. A sorbent cartridge for use in preparing samples for chemical analysis, comprising:
   a tip having a longitudinal axis and a distal tip having cavity walls that define an interior cavity extending along the axis with an opening at a distal end of the tip;
   a porous barrier in the cavity placed at a predetermined location in the tip to define a sorbent volume between the barrier, the cavity walls and the opening at the distal end of the tip, the barrier allowing processing fluids to pass through the barrier; and
   a slurry containing sorbent material in the sorbent volume and extending from the opening toward the barrier, the sorbent not being restrained by a porous barrier at the opening from being expelled from the opening, the sorbent material being selected for use in the chemical analysis and the barrier being selected to prevent passage of the sorbent material out of the sorbent volume, the sorbent material being adapted to pass into the opening with the slurry.

22. The sorbent cartridge of claim 21, wherein the cavity walls at the opening extend toward the longitudinal axis to form a lip that helps retain the sorbent in the cavity.

23. The sorbent cartridge of claim 21, wherein the tip forms a tapered cavity ending at the distal end.

24. The sorbent cartridge of claim 21, wherein the sorbent material substantially fills the sorbent volume.

25. The sorbent cartridge of claim 21, wherein the sorbent comprises a plurality of particles coated with a material that helps prevent the sorbent from sliding out the opening.

26. The sorbent cartridge of claim 25, wherein the particles are coated with propylene glycol.

27. The sorbent cartridge of claim 25, wherein the particles are coated with ethylene glycol.

28. The sorbent cartridge of claim 25, wherein the particles are coated with glycerol.

29. The sorbent cartridge of claim 21, wherein the sorbent comprises a plurality of particles filling between about 50–60% of the sorbent volume.

30. The sorbent cartridge of claim 21, further comprising a cap covering the opening and placed to prevent sorbent from passing out of the opening.

31. The sorbent cartridge of claim 21, wherein the sorbent material comprises particles having diameters and wherein the distal opening has a diameter of about 2 to about 10 times the maximum diameter of the particles.

32. A sorbent cartridge for use in preparing samples for chemical analysis, comprising:
   a tip having a longitudinal axis and a distal tip having cavity walls that define an interior cavity extending along the axis with an opening at a distal end of the tip;
   a porous barrier at not more than one location inside the cavity in the tip and defining a sorbent volume between the porous barrier, the cavity walls and the opening at the distal end of the tip, the porous barrier allowing processing fluids to pass through the barrier; and
   a slurry containing sorbent material in the sorbent volume and extending from the opening toward the barrier, the sorbent material being selected for use in the chemical analysis and the barrier being selected to prevent passage of the sorbent material out of the sorbent volume while allowing the passage of processing fluids through the porous barrier, the sorbent being sized to pass into the opening with the slurry and the opening having no porous barrier restraining the sorbent from passing out of the sorbent volume through the opening.

33. The sorbent cartridge of claim 32, wherein the tip is tapered toward the opening in the distal end of the tip.

34. The sorbent cartridge of claim 33, wherein the sorbent material substantially fills all of the sorbent volume.

35. The sorbent cartridge of claim 32, wherein the distal tip is conical.

36. The sorbent cartridge of claim 32, wherein the distal tip is tapered at least immediately adjacent the opening in tip.

37. The sorbent cartridge of claim 32, further comprising a removable cap.

38. A sorbent cartridge for use in preparing samples for chemical analysis, comprising:
a tip having a longitudinal axis and a distal tip having cavity walls that define a tapered interior cavity extending along the axis with an opening at a distal end of the tip;
a porous barrier at not more than one location inside the cavity in the tip and defining a sorbent volume between the porous barrier, the cavity walls and the opening at the distal end of the tip, the porous barrier allowing processing fluids to pass through the barrier; and
a slurry containing sorbent material in the sorbent volume and extending from the opening to the barrier, the sorbent material being selected for use in the chemical analysis and the barrier being selected to prevent passage of the sorbent material out of the sorbent volume while allowing the passage of processing fluids through the porous barrier, the sorbent being adapted to pass into the opening with the slurry, the opening having no porous barrier restraining the sorbent from passing into or out of the sorbent volume through the opening.

39. The sorbent cartridge of claim 38, further comprising a removable cap covering the opening.

40. A sorbent cartridge for use in preparing samples for chemical analysis, comprising:
a pipette tip having a longitudinal axis and a hollow distal tip with tapered walls defining an interior cavity extending along the axis and opening at a distal end of the tip which opening is not blocked by a porous barrier;
a porous barrier in the tapered cavity placed at a predetermined location in the tip to define a sorbent volume between the barrier, the cavity walls and the opening at the distal end of the tip, the barrier allowing processing fluids to pass through the barrier; and
a sorbent material in the sorbent volume, the sorbent material being selected for use in the chemical analysis and the barrier being selected to prevent passage of the sorbent material out of the sorbent volume, the sorbent material comprising a plurality of particles with a coating of a solvent on the particles that is sticky enough to cause the particles to stick together and resist passage out of the opening in the tip under the influence of gravitational forces while allowing sorbent to be expelled under pressure.

41. The sorbent cartridge of claim 40, wherein the solvent is one of glycol, ethylene glycol, or propylene.

42. The sorbent cartridge of claim 40, wherein the solvent includes a form of glycol.

43. A sorbent cartridge, comprising:
a pipette tip having an interior cavity in fluid communication with a distal opening located in the tip, the opening not being blocked by a porous barrier;
a filter placed in the tip and defining a predetermined volume between the barrier and the distal opening; and
a sorbent material substantially filling the volume, the filter retaining the sorbent material in the predetermined volume while allowing passage of processing fluids through the filter during use of the cartridge, the sorbent material comprising a plurality of particles having a coating of a solvent that is sticky enough to cause the particles of the sorbent material to stick together and resist passage out of the opening in the tip under the influence of gravitational forces while allowing sorbent to be expelled under pressure.

44. The sorbent cartridge of claim 43, wherein the solvent is one of glycol, ethylene glycol, or propylene.

45. The sorbent cartridge of claim 43, further comprising a removable cap covering the opening.

46. The sorbent cartridge of claim 43, wherein the solvent includes a form of glycol.

47. A sorbent cartridge for use in preparing fluid samples for chemical analysis, comprising:
a pipette tip with a first opening and a first porous barrier placed in the tip to define a sorbent volume of about 1 $\mu$ml or less between the porous barrier and the first opening, with no other porous barrier between the first porous barrier and the opening;
a plurality of sorbent particles in the sorbent volume coated with a solvent that wets the sorbent particles and can pass through the porous barrier during use of the pipette tip, the particles being loose enough to be expelled through the first opening by pressure after interacting with a fluid sample.

48. The sorbent cartridge of claim 47, wherein the solvent is sticky enough so the sorbent particles clump together and do not readily fall out of the first opening under the force of gravity but can be expelled through that opening under positive pressure.

49. The sorbent cartridge of claim 47, wherein the sorbent volume is filled by the sorbent particles.

* * * * *